United States Patent [19]
Ferruti et al.

[11] 4,379,091
[45] Apr. 5, 1983

[54] ESTERS OF ARYLPROPIONIC ACIDS ENDOWED WITH AN ANTI-INFLAMMATORY ACTIVITY

[75] Inventors: Paolo Ferruti; Ferdinando Danusso, both of Milan; Maria C. Tanzi, Monza; Giuseppe Quadro, Milan, all of Italy

[73] Assignee: Ausonia Farmaceutici s.r.l., Rome, Italy

[21] Appl. No.: 233,665

[22] Filed: Feb. 11, 1981

[30] Foreign Application Priority Data

Feb. 13, 1980 [IT] Italy ............................... 19879 A/80

[51] Int. Cl.³ ............................................. C07C 69/76
[52] U.S. Cl. ..................................... 548/472; 549/70; 560/52; 560/56; 560/100; 560/112; 424/283; 424/308

[58] Field of Search .................. 560/112, 100, 52, 56; 260/326.1; 549/70; 424/283, 308

[56] References Cited

U.S. PATENT DOCUMENTS 3,468,939   9/1969   Kaltenbronn ....................... 560/100
4,009,197   2/1977   Fried et al. .......................... 560/100

Primary Examiner—Paul J. Killos
Attorney, Agent, or Firm—Bucknam and Archer

[57] ABSTRACT

The present invention concerns tetraethylene glycol monoesters with 2-arylpropionic acids (known as anti-inflammatory agents). Said esters, while being endowed with the characteristics of low toxicity and gastric injuring effects shown by the related acids, differ advantageously from the latter because their anti-inflammatory activity is much more prolonged, and their bioavailability markedly better.

7 Claims, 1 Drawing Figure

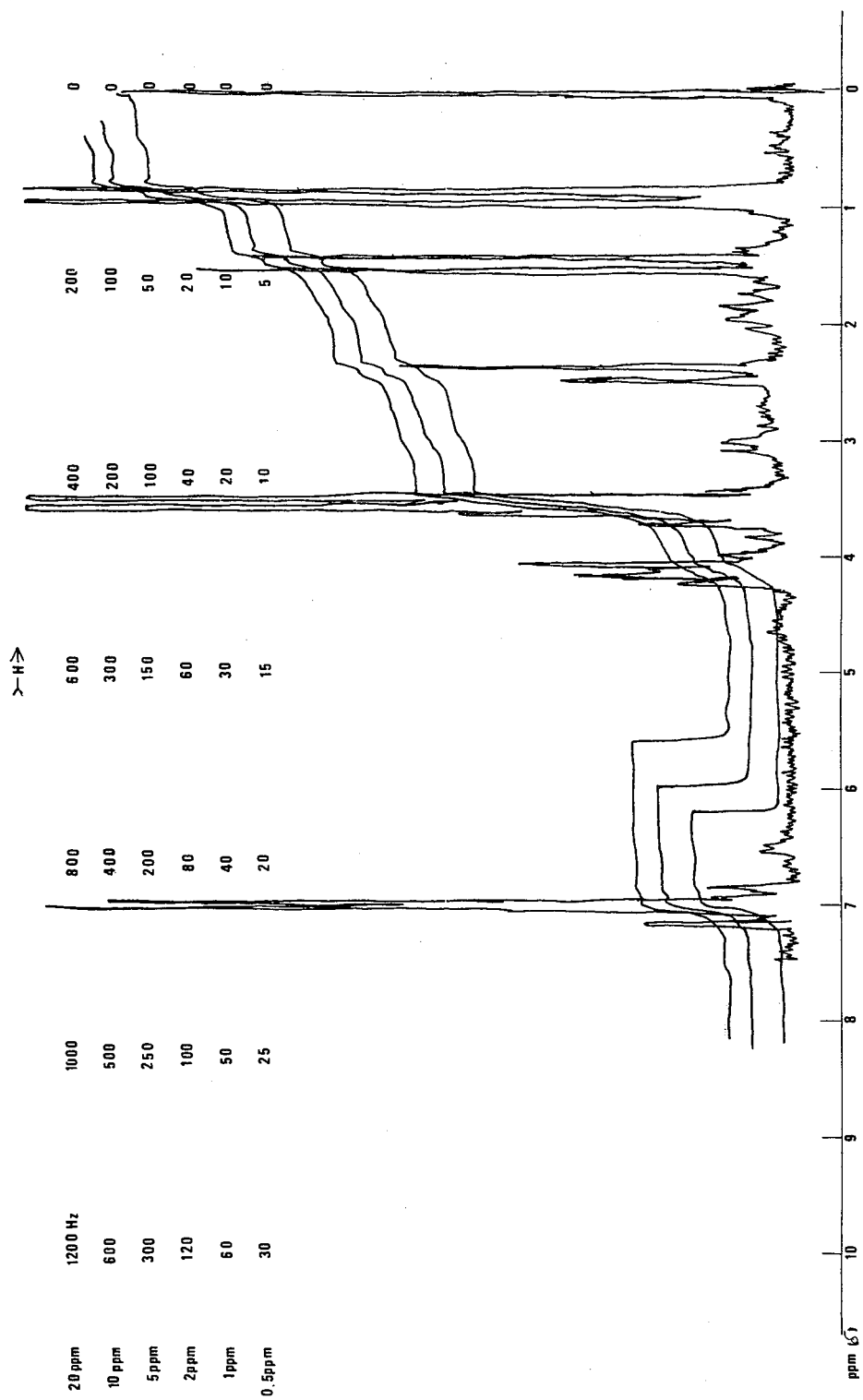

ESTERS OF ARYLPROPIONIC ACIDS ENDOWED WITH AN ANTI-INFLAMMATORY ACTIVITY

DESCRIPTION OF THE INVENTION

The present invention concerns new esters of arylpropionic acids characterized by the general formula (I)

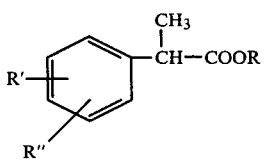

where R represents the $-(CH_2CH_2O)_3-CH_2-CH_2OH$ residue; R' may be a hydrogen atom, in which case R" represents the isobutyl, benzoyl, 2-thenoyl or 1-oxo-2-isoindolinyl residue or alternatively R' may be a phenyl group in which case R" represents a fluorine atom or still R' and R" may together represent a benzene ring orthocondensated on the former and carrying a methoxy group. Preferably, R' and R" are such that (I) represents esters of tetraethylene glycol with 2-(4-isobutyl-phenyl)-, 2-[4-2-(thenoyl)-phenyl]-, 2-[4-(1-oxo-2-isoindolinyl-phenyl]-, 2-(3-benzoyl-phenyl)-, 2-(3-fluoro-4-phenyl-phenyl) and 2-(6-methoxy-2-naphthyl)-propionic acids, all known for their anti-inflammatory properties. The present invention also concerns the enantiomers of the esters of formula (I).

The compounds (I), comparable to the corresponding acids with respect to their properties of low toxicity and gastric injuring effects, present an anti-inflammatory activity that, although showing an equivalent intensity, differs markedly for a more prolonged duration. This evidence represents a considerable advantage since the corresponding acids are characterized generally by a short-time action. Also pharmacokinetic investigations show a bioavailability markedly higher, even of a 100 percent rate, than that shown by the corresponding acids. Therefore, a further object of the present invention is represented by pharmaceutical compositions endowed with an anti-inflammatory activity, containing as active ingredient at least one ester of formula (I), in the form of a racemic or of enantiomers.

A further object of the present invention is represented by a procedure for the preparation of the esters (I), that consists in reacting compounds of formula (II)

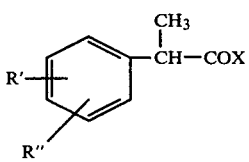

(wherein R' and R" have the above stated significance while X represents either a hydroxyl group or preferably an activating group such as alkoxy, Cl, 1-imidazolyl group or still a residue apt to form an anhydride function with the remaining moiety of the molecule) with an excess of tetraethylene glycol. Preferably, the compounds (II) are reacted with tetraethylene glycol, in a molar ratio at least equivalent to 1:3.5, in order to ensure the maximum yield of monoester.

The below reported example illustrates the invention, constituting however no limitation to its scope.

EXAMPLE

Monoester of 2-(4-isobutyl-phenyl)propionic acid with tetraethylene glycol

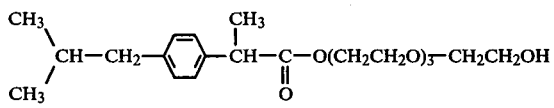

20 grams (0.09 moles) of 2-(4-isobutyl-phenyl) propionic acid (Ibuprofen) are dissolved in 250 ml of anhydrous $CHCl_3$. The resulting solution is added with 20 g of carbonyl-diimidazole (CDI, 0.12 moles, 33 percent excess) under agitation, at room temperature. As soon as the effervescence is terminated (30 minutes approximately), the reaction mixture is added with 55.2 ml of tetraethylene glycol (0.32 moles, 250 percent excess approximately), previously dried on $CaSO_4$. The reaction is caused to occur in a thermostatized bath at 60° C. for 48 h.

The solution is concentrated in a rotary evaporator, and diluted thereafter with ethyl ether (250–300 ml). The ether solution is then washed two times with 100 ml of water, two times with 100 ml of 0.1 N HCl, two further times with 100 ml of water, two times with 100 ml of 0.1 N NaOH, and finally three times with 100 ml of water.

After drying on $Na_2SO_4$, the resulting solution is filtered and evaporated to dryness. The residue is purified by washing with anhydrous n-heptane (500 ml approximately), duly cooling in order to reduce to a minimum the solubility of the product, appreciable also in apolar solvents. n-Heptane is then decanted, and the product is dried under vacuum (0.1 mmHg). 80 percent yield.

On the basis of the NMR spectrum (see attached figure), the overall rate of esterification results to correspond to 50 percent approximately in weight of 2-(4-isobutyl-phenyl) propionic acid likely to be liberated. Said datum is comparable with the one resulting from the indirect titration (theoretical:1.319 meq; practical:1.33 meq, equivalent to 50.4 percent of acid likely to be liberated); moreover, the direct titration states the absence of unbound acid.

The resulting product (that, for brevity's sake shall be indicated from now on with the code name MR-653) is practically insoluble in water, and soluble on the other hand in methanol, diethyl ether, acetone and chloroform.

The $MeOH/CHCl_3$/glacial acetic acid (70:35:4) mixture was used for the elution on 60 Merck Kieselgel plates.

MR-653, the starting acid and tetraethylene glycol show the following retention coefficients:

|  | $R_f$ |
|---|---|
| MR-653 | 0.8 |
| Acid | 0.78 |
| Tetraethylene glycol | 0.6 |

CHROMATOGRAPHIC TESTS

A single spot characterizes the presence of MR-653. TLC does not show in any case the presence of unbound 2-(4-isobutyl-phenyl) propionic acid. A related perfect reproducibility was observed repeating the preparations of the compounds MR-653. This evidence also proved valid in all the cases in which the chloride of 2-(4-isobutyl-phenyl)-propionic acid or its mixed anhydride with ethyl chlorocarbonate are used in replacement of imidazolide.

The pharmacotoxicologic properties of the esters (I) are herein described on the basis of the example provided by MR-653.

ACUTE TOXICITY: in the mouse, the oral LD 50 of MR-653 proved higher than 2000 mg/kg.

ANTI-INFLAMMATORY ACTIVITY

The anti-inflammatory activity of MR-653 was assessed versus the one of ibuprofen, ie 2-(4-isobutyl-phenyl)-propionic acid, at equimolar doses by the carrageenin edema test in the rat (Wistar males and females, bodyweight 160–200 g, twelve animals per compound and per experiment). 1 percent carrageenin in saline was given, at the rate of 0.1 ml subcutaneously, into the plantar area of the left paw.

Ibuprofen was given at doses of 100 mg/kg/os (in 5 percent gum arabic); MR-653 in doses equivalent to ibuprofen 100 mg/kg/os, ie 200 mg/kg/os respectively.

The compounds were administered 1, 3 and 6 hours respectively before the carrageenin injection; the related values were always read 4 hours after the carrageenin injection, duly assessing the percent swelling of the paw versus the value at the time 0 (carrageenin inocula). The results are expressed as percent protection considering the swelling in the control group as equal to 100.

The protection exerted by the two compounds, versus the edema induced by carrageenin, proved rapid and effective. A comparable peak of activity is observed for both treatments around the first hour; this peak, while undergoing in the case of ibuprofen a rapid and progressive decrease even starting from the second hour, proves on the contrary markedly slower in the case of MR-653, with a typical action prolonged in the course of time, as results from the attached Table 1.

TABLE 1

| Percent protection from the carrageenin edema considering the control groups as equal to 100 | | | | | |
|---|---|---|---|---|---|
| | Detection after hours | | | | |
| Drug | 1 | 2 | 3 | 4 | 6 |
| Ibuprofen | 60 | 44 | 28 | 24 | 20 |
| MR-653 | 64 | 59 | 47 | 44 | 34 |

ANALGESIC ACTIVITY

Abdominal squirmings were induced by an intraperitoneal injection in saline, given at the dose of 4 mg/kg/20 ml.

The compounds ibuprofen and MR-653 had been given one our before, orally, at the dose of 100 mg/kg (equimolar doses). In the course of the 20 minutes subsequent to the injection of phenylquinone, all animals were observed in order to detect any squirming: the animals, presenting with no squirming, were considered as protected. A 20 percent protection (10 animals per group), versus the control group, was observed for both products.

Acetylcholine Test

Squirmings were induced by an intraperitoneal injection of acetylcholine (200 ml; 0.5 ml per mouse); both compounds were given orally one hour before the administration of acetylcholine at the dose of 10 mg/kg, in equimolar doses. After the adminisration of acetylcholine the animals were observed for the subsequent 4 minutes, and considered protected when presenting with no squirming. The results reported below were obtained in comparison with the control group:

Ibuprofen: 50 percent protection
MR-653: 48 percent protection

Gastric Injuring Effects

The possible gastric injuring effect of MR-653, versus ibuprofen, was assessed on Wistar rats of either sex, bodyweight ranging between 160 and 200 g, fasted for 24 hours at the time of treatment. The compounds were given intraperitoneally at the equimolar dose of 500 mg/kg.

The animals were killed 5 hours after the treatment in order to assess the conditions of the gastric mucosa, and the possible presence of bleedings and ulcers.

Results

A punctiform ulcer was observed in 14 percent of the cases in the group given ibuprofen; stomachs were presenting with an almost normal mucosa with a fair quantity of a yellowish foamy secretion.

A comparable percent incidence of ulcerogenic punctiform episodes (16 percent), associated with the presence of a mildly hyperemic peritoneal exudate, was also observed in the group given MR-653.

PHARMACOKINETICS

The plasma kinetics of MR-653 was assessed, following oral administration, in the male albino rat, Wistar strain, bodyweight of 180–220 grams. Since this compound liberates in the body a certain amount of ibuprofen, the kinetics of the latter drug, at the doses of 58.8 mg/kg and 19.2 mg/kg, was also assessed. In the direct case of ibuprofen plasma kinetics was also investigated after intraperitoneal administration for the purpose of being provided with an assessment of the rate of the intestinal absorption of this drug. The investigational drugs were given by oral gavage, suspended in 0.5 percent gum arabic; an analogous suspension was used in the case of the intraperitoneal administration.

Blood withdrawals from the experimental animals were made from a sublingual vein according to the procedure described by M. Ferro Milone and P. Barbiera (Atti della Soc.It.Science Veterinarie, 1974, 28, 394). The plasma determination of ibuprofen was carried out by a gas chromatographic method, according to the procedure described by F. M. Runci and G. Segre (Recent Development in Chromatography and Electrophoresis, A. Frigerio, L. Renoz Eds., Elsevier, Amsterdam, 1979, p.199).

Table 2 shows the plasma kinetic patterns of ibuprofen after oral and intraperitoneal administration of 58.8 mg/kg.

If the intraperitoneal kinetics can be assimilated to the intravenous kinetics, it can be expressed by a biexponential equation, ie $$X(T) = 468e^{-2.1t} + 32e^{-0.23t}$$

where X=concentration in mcg/ml and t=hours.

The half-life, calculated on the basis of the second component, results to be equivalent to 3 hours approximately.

The AUC (areas under the curves) are on first approximation (for times up to the 7th hour) equivalent to 190 (os) and 325 (ip) with ratio equivalent to a 60 percent rate.

Table 2 also shows the kinetics of MR-653; the ibuprofen content is such that the dose used of MR-653 (120 mg/kg) corresponds to 58.8 mg/kg of ibuprofen.

On the basis of the content of ibuprofen, the plasma curves were compared with the curves provided by the administrations of 58.8 mg/kg of ibuprofen.

A line going through the peaks (at the first hour) of the plasma levels of ibuprofen was plotted in order to better compare the kinetic patterns. It could be therefore seen, on the basis of this line, that the value results to be markedly higher in the case of MR-653. This compound, therefore, shows an increased bioavailability (ranging on a 100 percent level, as can be assumed by extrapolation).

PHARMACOKINETICS

TABLE 2—Plasma concentrations (mcg/ml) and standard deviation of ibuprofen in the male rat after intraperitoneal and oral administration, and of MR-653 given orally.

hour. Actually, while in the case of ibuprofen the anti-inflammatory activity consists of a curve effect with highly marked drops, the activity of MR-653 proves quite prolonged with values still markedly high until the 6th hour, higher in fact, in a 48 percent rate, than those encountered in the case of ibuprofen.

This higher efficacy, especially in the long intervals, is also confirmed by the tests of pharmacokinetics that demonstrate the higher bioavailability of MR-653 with respect to ibuprofen for an approximate 100 percent rate.

We claim:

1. The tetraethylene glycol monoester with 2-(4-isobutyl-phenyl) propionic acid.
2. Tetraethylene glycol monoester with 2-[4-(2-thenoyl)phenyl]propionic acid.
3. Tetraethylene glycol monoester with 2-[4-(1-oxo-2-isoindolinyl)phenyl]propionic acid.
4. Tetraethylene glycol monoester with 2-(3-benzoyl-phenyl) propionic acid.
5. Tetraethylene glycol monoester with 2-(3-fluoro-4-phenyl-phenyl) propionic acid.
6. Tetraethylene glycol monoester with 2-(6-methoxy-2-naphthyl) propionic acid.
7. A pharmaceutical composition endowed with an anti-inflammatory and analgesic activity, which contains as the active ingredient, at least one ester, which is

| Compound | Dose given mg/kg | hours | | | | |
|---|---|---|---|---|---|---|
| | | 0.5 | 1 | 2 | 5 | 7 |
| Ibuprofen i.p. | 58.8 | 215.2 ± 33.4 | 104.7 ± 12.4 | 18.3 ± 11.0 | | 6.2 ± 2.4 |
| Ibuprofen os | 58.8 | | 71.7 ± 23.6 | 32.2 ± 7.7 | 12.1 ± 22 | 9.1 ± 1.5 |
| MR-653 os | 120* | | 118.4 ± 20.7 | 76.6 ± 12.9 | 45.2 ± 23.7 | 36.3 ± 11.3 |

*correspondent to 58.8 mg of Ibuprofen

It appears evident from the summary of the results that MR-653, compared with ibuprofen at equimolar doses exerts, although maintaining practically unchanged values of toxicity and gastric injuring effects, a better anti-inflammatory activity that becomes evident with an earlier onset of effects while higher values are kept in the course of time, especially after the second 2-(4-isobutyl-phenyl) propionic acid, 2-[4-(2-thenoyl)-phenyl]propionic acid, 2-[4-(1-oxo-2-isoindolinyl)-phenyl]propionic acid, 2-(3-benzoyl-phenyl) propionic acid, 2-(3-fluoro-4-phenyl-phenyl) propionic acid, or 2-(6-methoxy-2-naphthyl) propionic acid, in the form of a racemic or of an enantiomer.

* * * * *